Sept. 28, 1965 E. S. BOERNER Plant Pat. 2,555
CHRYSANTHEMUM PLANT
Filed June 18, 1964
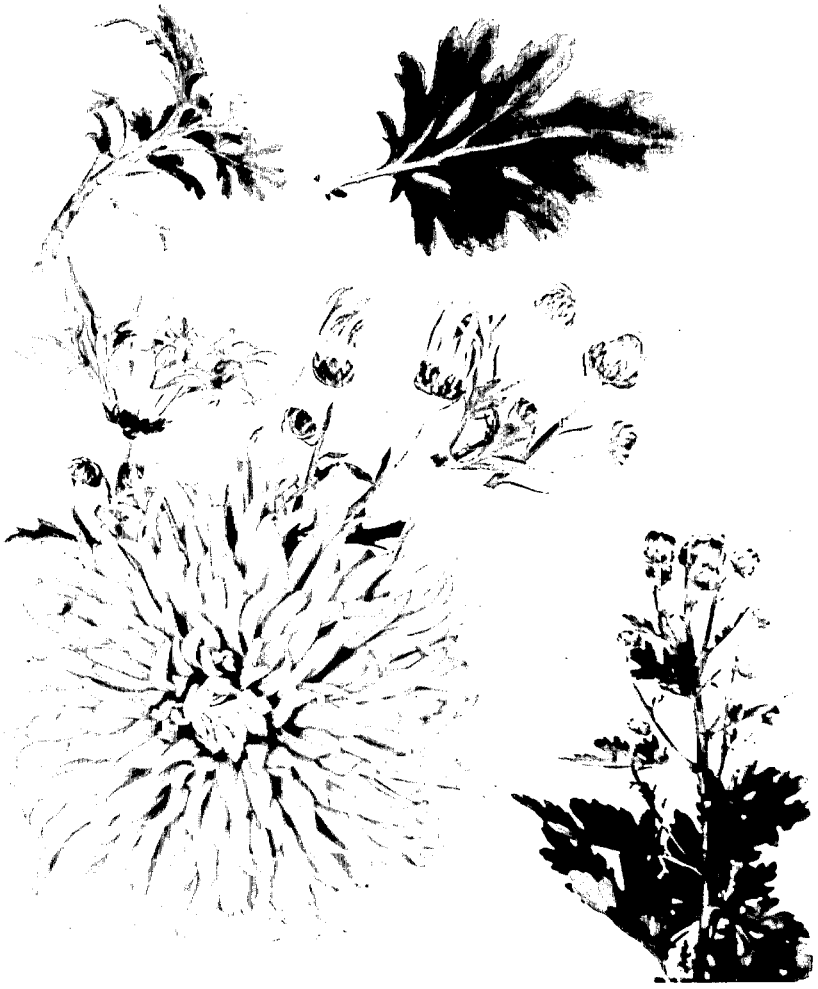
Inventor.
E. S. Boerner
By: Robb & Robb
Attorneys.

United States Patent Office

Plant Pat. 2,555
Patented Sept. 28, 1965

2,555
CHRYSANTHEMUM PLANT

Eugene S. Boerner, Newark, N.Y., assignor to Jackson & Perkins Company, Newark, N.Y., a corporation of New York Filed June 18, 1964, Ser. No. 376,283
1 Claim. (Cl. Plt.—76)

The present invention relates to a new and distinct variety of chrysanthemum plant of the shaggy decorative class, which was originated by me by crossing the chrysanthemum variety known as "Pink Seagull" (Plant Patent No. 1,820) with the chrysanthemum variety known as "Sandpiper" (Plant Patent No. 1,932).

The primary objective of this breeding was to produce a new chrysanthemum variety having a flower form and size characteristic of the parent variety "Pink Seagull" combined with the free flowering habit characteristic of the parent variety "Sandpiper." This objective was fully achieved along with other desirable improvements, as evidenced by the following unique combination of characteristics which are outstanding in the new variety and distinguish it from its parents, as well as from all other varieties of which I am aware:

(1) A low compact habit of growth;
(2) A free flowering habit;
(3) Large flower size; and
(4) A distinctive and attractive general color tonality of the flowers corresponding to Light Rosolane Purple, lightly overcast with Spinel Pink.

Asexual reproduction of the new variety by both top cuttings and underground runners, as performed at Newark, New York, shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in a color illustration of this character, as well as a typical specimen stem which is depicted in black and white for the purpose of illustrating the form and habit of growth of the plant.

The following is a detailed description of the new variety, with color terminology in accordance with Ridgway's Color Standards and Nomenclature:

Parentage: Seedling.
*Seed parent.*—"Pink Seagull."
*Pollen parent.*—"Sandpiper."
Classification: Shaggy decorative.
Growth: Free.
Location where observations made: Outdoors at Newark, New York, in the early afternoon during the first part of the month of October.

Cold resistance: Winter hardy in northern New York State.
Blooming period: From the end of September until freezing weather in northern New York State.
Bud:
*Color.*—When petals first divide—Pale Lilac, Plate 37, very lightly overcast with Tourmaline Pink, Plate 38. When petals begin to unfurl—Daphne Pink, Plate 38, with lower half of petals lightly overcast with Pale Persian Lilac, Plate 38. When half-blown: inside—Amaranth Purple, Plate 12; outside—Light Pinkish-Lilac, Plate 37, very lightly overcast with Pale Rhodonite Pink, Plate 38.
*Peduncle.*—Color—Light Hellebore Green, Plate 17. Strength—strong.
Bloom:
*Size.*—6 inches in diameter.
*Stem.*—Strong.
*Form.*—Shaggy decorative.
*Petalage.*—Double.
*Color.*—Center of flower—Spinel Pink, Plate 26, with upper half of petals lightly overcast with Light Rosolane Purple, Plate 26. Outer petals—Spinel Pink, Plate 26, overcast with Pale Rosolane Purple, Plate 26. Base of petals—Clear Dull Green-Yellow, Plate 17. Inside of petals—Light Rosolane Purple, Plate 26, lightly overcast with Spinel Pink, Plate 26. Reverse of petals—Pale Persian Lilac, Plate 38, very lightly overcast with Persian Lilac, Plate 38.
*Petals.*—Texture—medium. Form—oval.
*Fragrance.*—Characteristic chrysanthemum.

*Plant*

Form: Low; compact.
Growth: Free.
Foliage:
*Size.*—Medium.
*Quantity.*—Normal.
*Color.*—Upper side—Varley's Green, Plate 18. Reverse side—Light Bice Green, Plate 17.
*Texture.*—Leathery.

I claim:

A new and distinct variety of chrysanthemum plant of the shaggy decorative class, substantially as herein shown and described, characterized particularly as to novelty by the unique combination of a low and compact habit of growth, a free flowering habit, large flower size, and a distinctive and attractive general color tonality of the flowers corresponding to Light Rosolane Purple, lightly overcast with Spinel Pink.

No references cited.

ABRAHAM G. STONE, *Primary Examiner.*